(12) United States Patent
Allavatam

(10) Patent No.: US 10,758,138 B2
(45) Date of Patent: Sep. 1, 2020

(54) USE OF DETECTION PROFILES IN AN IMPLANTABLE MEDICAL DEVICE

(71) Applicant: CAMERON HEALTH, INC., St. Paul, MN (US)

(72) Inventor: Venugopal Allavatam, Maple Grove, MN (US)

(73) Assignee: CAMERON HEALTH, INC., St. Paul, MN (US)

( * ) Notice: Subject to any disclaimer, the term of this patent is extended or adjusted under 35 U.S.C. 154(b) by 537 days.

(21) Appl. No.: 15/384,144

(22) Filed: Dec. 19, 2016

(65) Prior Publication Data

US 2017/0095175 A1 Apr. 6, 2017

Related U.S. Application Data

(63) Continuation of application No. 14/815,267, filed on Jul. 31, 2015, now Pat. No. 9,554,714.
(Continued)

(51) Int. Cl.
*A61N 1/37* (2006.01)
*A61B 5/04* (2006.01)
(Continued)

(52) U.S. Cl.
CPC ........ *A61B 5/04012* (2013.01); *A61B 5/0422* (2013.01); *A61B 5/0472* (2013.01);
(Continued)

(58) Field of Classification Search
CPC ... A61B 5/024; A61B 5/04012; A61B 5/0402; A61B 5/0452; A61B 5/04525; A61B 5/0456; A61B 5/0468; A61B 5/0472; A61B 5/7203; A61B 5/7221; A61B 5/7246; A61N 1/37; A61N 1/3702; A61N 1/3704
See application file for complete search history.

(56) References Cited

U.S. PATENT DOCUMENTS 4,184,493 A 1/1980 Langer et al.
4,300,567 A 11/1981 Kolenik et al.
(Continued)

FOREIGN PATENT DOCUMENTS

CN 1819855 A 8/2006
CN 1829554 A 9/2006
(Continued)

OTHER PUBLICATIONS

Gunderson et al. "An Algorithm to Predict Implantable Cardioverter-Defibrillator Lead Failure." JACC, 44:9, pp. 1898-1902, Nov. 2004.
(Continued)

*Primary Examiner* — Eugene T Wu
(74) *Attorney, Agent, or Firm* — Seager, Tufte & Wickhem LLP

(57) ABSTRACT

Implantable medical device systems and methods configured to use a detection profile selected from among a plurality of detection profiles to define a detection threshold for identifying cardiac events, in which a close call definition is used to determine which of the plurality of detection profiles is to be chosen. Upon identifying a close call, in which an overdetection nearly occurred but did not actually take place, a relatively less sensitive detection profile is chosen.

12 Claims, 9 Drawing Sheets

Related U.S. Application Data

(60) Provisional application No. 62/037,288, filed on Aug. 14, 2014.

(51) Int. Cl.
  *A61B 5/042* (2006.01)
  *A61B 5/00* (2006.01)
  *A61B 5/0472* (2006.01)
  *A61B 5/0452* (2006.01)

(52) U.S. Cl.
  CPC ............ *A61B 5/686* (2013.01); *A61N 1/3704* (2013.01); *A61B 5/042* (2013.01); *A61B 5/04017* (2013.01); *A61B 5/0452* (2013.01)

(56) References Cited

U.S. PATENT DOCUMENTS

| | | |
|---|---|---|
| 4,407,288 A | 10/1983 | Langer et al. |
| 4,450,527 A | 5/1984 | Sramek |
| 4,457,315 A | 7/1984 | Bennish |
| 4,589,420 A | 5/1986 | Adams et al. |
| 4,595,009 A | 6/1986 | Leinders |
| 4,679,144 A | 7/1987 | Cox et al. |
| 4,693,253 A | 9/1987 | Adams |
| 4,750,494 A | 6/1988 | King |
| 4,779,617 A | 10/1988 | Whigham |
| 4,940,054 A | 7/1990 | Grevis et al. |
| 4,979,110 A | 12/1990 | Albrecht et al. |
| 4,989,602 A | 2/1991 | Sholder et al. |
| 5,000,189 A | 3/1991 | Throne et al. |
| 5,105,810 A | 4/1992 | Collins et al. |
| 5,117,824 A | 6/1992 | Keimel et al. |
| 5,184,616 A | 2/1993 | Weiss |
| 5,193,535 A | 3/1993 | Bardy et al. |
| 5,215,098 A | 6/1993 | Steinhaus et al. |
| 5,217,021 A | 6/1993 | Steinhaus et al. |
| 5,240,009 A | 8/1993 | Williams |
| 5,271,411 A | 12/1993 | Ripley et al. |
| 5,273,049 A | 12/1993 | Steinhaus et al. |
| 5,280,792 A | 1/1994 | Leong et al. |
| 5,299,119 A | 3/1994 | Kraf et al. |
| 5,313,953 A | 5/1994 | Yomtov et al. |
| 5,331,966 A | 7/1994 | Bennett et al. |
| 5,339,820 A | 8/1994 | Henry et al. |
| 5,342,402 A | 8/1994 | Olson et al. |
| 5,342,407 A | 8/1994 | Dahl et al. |
| 5,351,686 A | 10/1994 | Steuer et al. |
| 5,351,696 A | 10/1994 | Riff et al. |
| 5,376,104 A | 12/1994 | Sakai et al. |
| 5,400,795 A | 3/1995 | Murphy et al. |
| 5,423,326 A | 6/1995 | Wang et al. |
| 5,447,519 A | 9/1995 | Peterson |
| 5,464,431 A | 11/1995 | Adams et al. |
| 5,470,342 A | 11/1995 | Mann et al. |
| 5,486,199 A | 1/1996 | Kim et al. |
| 5,513,644 A | 5/1996 | McClure et al. |
| 5,522,852 A | 6/1996 | White et al. |
| 5,534,019 A | 7/1996 | Paspa |
| 5,545,186 A | 8/1996 | Olson et al. |
| 5,558,098 A | 9/1996 | Fain |
| 5,564,430 A | 10/1996 | Jacobson et al. |
| 5,607,455 A | 3/1997 | Armstrong |
| 5,620,466 A | 4/1997 | Haefner et al. |
| 5,658,317 A | 8/1997 | Haefner et al. |
| 5,676,690 A | 10/1997 | Norén |
| 5,685,315 A | 11/1997 | McClure et al. |
| 5,702,425 A | 12/1997 | Wickham |
| 5,709,215 A | 1/1998 | Perttu et al. |
| 5,755,738 A | 5/1998 | Kim et al. |
| 5,776,168 A | 7/1998 | Gunderson |
| 5,779,645 A | 7/1998 | Olson et al. |
| 5,817,134 A | 10/1998 | Greenhut et al. |
| 5,827,197 A | 10/1998 | Bocek et al. |
| 5,857,977 A | 1/1999 | Caswell et al. |
| 5,876,350 A | 3/1999 | Lo et al. |
| 5,891,048 A | 4/1999 | Nigam et al. |
| 5,991,657 A | 11/1999 | Kim |
| 6,029,086 A | 2/2000 | Kim et al. |
| 6,041,251 A | 3/2000 | Kim et al. |
| 6,047,210 A | 4/2000 | Kim et al. |
| 6,052,617 A | 4/2000 | Kim |
| 6,058,328 A | 5/2000 | Levine et al. |
| 6,095,987 A | 8/2000 | Shmulewitz et al. |
| 6,115,628 A | 9/2000 | Stadler et al. |
| 6,144,879 A | 11/2000 | Gray |
| 6,148,230 A | 11/2000 | KenKnight |
| 6,223,078 B1 | 4/2001 | Marcovecchio |
| 6,230,055 B1 | 5/2001 | Sun et al. |
| 6,236,882 B1 | 5/2001 | Lee et al. |
| 6,240,313 B1 | 5/2001 | Esler |
| 6,266,554 B1 | 7/2001 | Hsu et al. |
| 6,280,462 B1 | 8/2001 | Hauser et al. |
| 6,308,095 B1 | 10/2001 | Hsu et al. |
| 6,334,071 B1 | 12/2001 | Lu |
| 6,377,844 B1 | 4/2002 | Graen |
| 6,381,493 B1 | 4/2002 | Stadler et al. |
| 6,393,316 B1 | 5/2002 | Gillberg et al. |
| 6,397,100 B2 | 5/2002 | Stadler et al. |
| 6,411,844 B1 | 6/2002 | Kroll et al. |
| 6,438,410 B2 | 8/2002 | Hsu et al. |
| 6,449,503 B1 | 9/2002 | Hsu |
| 6,493,579 B1 | 12/2002 | Gilkerson et al. |
| 6,493,584 B1 | 12/2002 | Lu |
| 6,505,068 B2 | 1/2003 | Bonnet et al. |
| 6,516,225 B1 | 2/2003 | Florio |
| 6,561,984 B1 | 5/2003 | Turcott |
| 6,567,691 B1 | 5/2003 | Stadler |
| 6,574,505 B1 | 6/2003 | Warren |
| 6,575,912 B1 | 6/2003 | Turcott |
| 6,587,720 B2 | 7/2003 | Hsu et al. |
| 6,625,490 B1 * | 9/2003 | McClure ............ A61N 1/3704 607/9 |
| 6,643,549 B1 | 11/2003 | Bradley et al. |
| 6,647,292 B1 | 11/2003 | Bardy et al. |
| 6,684,100 B1 | 1/2004 | Sweeney et al. |
| 6,699,200 B2 | 3/2004 | Cao et al. |
| 6,708,058 B2 | 3/2004 | Kim et al. |
| 6,708,062 B2 | 3/2004 | Ericksen et al. |
| 6,721,597 B1 | 4/2004 | Bardy et al. |
| 6,728,572 B2 | 4/2004 | Hsu et al. |
| 6,731,978 B2 | 5/2004 | Olson et al. |
| 6,745,068 B2 | 6/2004 | Koyrakh et al. |
| 6,754,528 B2 | 6/2004 | Bardy et al. |
| 6,889,079 B2 | 5/2005 | Bocek et al. |
| 6,892,092 B2 | 5/2005 | Palreddy et al. |
| 6,909,916 B2 | 6/2005 | Spinelli et al. |
| 6,950,702 B2 | 9/2005 | Sweeney |
| 7,016,730 B2 | 3/2006 | Ternes |
| 7,020,523 B1 | 3/2006 | Lu et al. |
| 7,027,856 B2 | 4/2006 | Zhou et al. |
| 7,027,858 B2 | 4/2006 | Cao et al. |
| 7,027,862 B2 | 4/2006 | Dahl et al. |
| 7,031,764 B2 | 4/2006 | Schwartz et al. |
| 7,062,314 B2 | 6/2006 | Zhu et al. |
| 7,062,315 B2 | 6/2006 | Koyrakh et al. |
| 7,062,322 B2 | 6/2006 | Stadler et al. |
| 7,076,289 B2 | 7/2006 | Sarkar et al. |
| 7,085,599 B2 | 8/2006 | Kim et al. |
| 7,103,412 B1 | 9/2006 | Kroll |
| 7,117,035 B2 | 10/2006 | Wagner et al. |
| 7,123,954 B2 | 10/2006 | Narayan et al. |
| 7,149,575 B2 | 12/2006 | Ostroff et al. |
| 7,155,282 B1 * | 12/2006 | Min ..................... A61B 5/0452 607/28 |
| 7,162,301 B2 | 1/2007 | Kim et al. |
| 7,167,747 B2 | 1/2007 | Gunderson et al. |
| 7,184,815 B2 | 2/2007 | Kim et al. |
| 7,184,818 B2 | 2/2007 | Kim et al. |
| 7,191,004 B2 | 3/2007 | Kim et al. |
| 7,194,302 B2 | 3/2007 | Bardy et al. |
| 7,218,966 B2 | 5/2007 | Haefner |
| 7,236,819 B2 | 6/2007 | Brockway et al. |
| 7,248,921 B2 | 7/2007 | Palreddy et al. |

(56) References Cited

U.S. PATENT DOCUMENTS

| | | |
|---|---|---|
| 7,266,409 B2 | 9/2007 | Gunderson |
| 7,283,863 B2 | 10/2007 | Gunderson et al. |
| 7,302,294 B2 | 11/2007 | Kamath et al. |
| 7,330,757 B2 | 2/2008 | Ostroff et al. |
| 7,346,392 B2 | 3/2008 | KenKnight |
| 7,376,458 B2 | 5/2008 | Palreddy et al. |
| 7,379,772 B2 | 5/2008 | Bardy et al. |
| 7,386,342 B1 | 6/2008 | Falkenberg et al. |
| 7,392,085 B2 | 6/2008 | Warren et al. |
| 7,444,182 B2 | 10/2008 | Ostroff et al. |
| 7,447,540 B1 | 11/2008 | Nabutovsky et al. |
| 7,467,009 B2 | 12/2008 | Palreddy et al. |
| 7,477,935 B2 | 1/2009 | Palreddy et al. |
| 7,496,408 B2 | 2/2009 | Ghanem et al. |
| 7,496,409 B2 | 2/2009 | Greenhut et al. |
| 7,499,750 B2 | 3/2009 | Haefner et al. |
| 7,522,959 B2 | 4/2009 | Hauser et al. |
| 7,546,159 B1 | 6/2009 | Nabutovsky et al. |
| 7,555,335 B2 | 6/2009 | Kamath et al. |
| 7,559,900 B2 | 7/2009 | Gillberg |
| 7,567,835 B2 | 7/2009 | Gunderson et al. |
| 7,570,997 B2 | 8/2009 | Lovett et al. |
| 7,593,771 B2 | 9/2009 | Yonce et al. |
| 7,623,913 B2 | 11/2009 | Phillips |
| 7,623,916 B2 | 11/2009 | Julian |
| 7,655,014 B2 | 2/2010 | Ko et al. |
| 7,682,316 B2 | 3/2010 | Anderson et al. |
| 7,684,864 B2 | 3/2010 | Olson et al. |
| 7,715,906 B2 | 5/2010 | Krause et al. |
| 7,734,345 B2 | 6/2010 | Cinbis |
| 7,761,142 B2 | 7/2010 | Ghanem et al. |
| 7,774,049 B2 | 8/2010 | Ghanem et al. |
| 7,783,354 B2 | 8/2010 | Gunderson |
| 7,792,571 B2 | 9/2010 | Sweeney et al. |
| 7,797,036 B2 | 9/2010 | Zhang et al. |
| 7,801,594 B1 | 9/2010 | Higham |
| 7,865,233 B2 | 1/2011 | Haefner |
| 7,894,894 B2 | 2/2011 | Stadler et al. |
| 7,904,142 B2 | 3/2011 | Kim et al. |
| 7,904,153 B2 | 3/2011 | Greenhut et al. |
| 7,907,993 B2 | 3/2011 | Ghanem et al. |
| 8,160,686 B2 | 4/2012 | Allavatam et al. |
| 8,160,687 B2 | 4/2012 | Warren et al. |
| 8,160,697 B2 | 4/2012 | Warren et al. |
| 8,265,737 B2 | 9/2012 | Warren et al. |
| 8,265,749 B2 | 9/2012 | Allavatam et al. |
| 8,494,630 B2 | 7/2013 | Palreddy et al. |
| 8,565,878 B2 | 10/2013 | Allavatam et al. |
| 8,588,895 B2 | 11/2013 | Sanghera et al. |
| 8,588,896 B2 | 11/2013 | Allavatam et al. |
| 8,600,489 B2 | 12/2013 | Warren et al. |
| 8,626,280 B2 | 1/2014 | Allavatam et al. |
| 8,744,555 B2 | 6/2014 | Allavatam et al. |
| 2003/0204215 A1 | 10/2003 | Gunderson et al. |
| 2004/0049120 A1 | 3/2004 | Cao et al. |
| 2004/0215239 A1 | 10/2004 | Favet et al. |
| 2004/0215240 A1 | 10/2004 | Lovett et al. |
| 2004/0220628 A1 | 11/2004 | Wagner |
| 2004/0230229 A1 | 11/2004 | Lovett et al. |
| 2005/0107838 A1 | 5/2005 | Lovett et al. |
| 2005/0131464 A1 | 6/2005 | Heinrich et al. |
| 2005/0154421 A1 | 7/2005 | Ousdigian |
| 2006/0116595 A1 | 6/2006 | Palreddy et al. |
| 2006/0116725 A1 | 6/2006 | Palreddy et al. |
| 2006/0122676 A1 | 6/2006 | Ko et al. |
| 2006/0167502 A1 | 7/2006 | Haefner |
| 2006/0167503 A1 | 7/2006 | Warren et al. |
| 2006/0167504 A1 | 7/2006 | Warren et al. |
| 2006/0235476 A1 | 10/2006 | Gunderson et al. |
| 2006/0241701 A1 | 10/2006 | Markowitz et al. |
| 2007/0032829 A1 | 2/2007 | Ostroff |
| 2007/0049975 A1 | 3/2007 | Cates et al. |
| 2007/0135847 A1 | 6/2007 | Kenknight |
| 2007/0142736 A1 | 6/2007 | Cazares et al. |
| 2007/0156190 A1 | 7/2007 | Cinbis |
| 2007/0179539 A1 | 8/2007 | Degroot et al. |
| 2007/0179540 A1 | 8/2007 | Stegemann et al. |
| 2007/0232944 A1 | 10/2007 | Ghanem et al. |
| 2007/0232945 A1 | 10/2007 | Kleckner et al. |
| 2007/0232948 A1 | 10/2007 | Stadler et al. |
| 2007/0233198 A1 | 10/2007 | Ghanem et al. |
| 2007/0276445 A1 | 11/2007 | Sanghera et al. |
| 2008/0015647 A1 | 1/2008 | Palreddy et al. |
| 2008/0077030 A1 | 3/2008 | Ostroff et al. |
| 2008/0082014 A1 | 4/2008 | Cao et al. |
| 2008/0086174 A1 | 4/2008 | Libbus et al. |
| 2008/0091242 A1 | 4/2008 | Kamath et al. |
| 2008/0132965 A1 | 6/2008 | Ostroff et al. |
| 2008/0161870 A1 | 7/2008 | Gunderson |
| 2008/0172098 A1 | 7/2008 | Gunderson |
| 2008/0183085 A1 | 7/2008 | van Oort et al. |
| 2008/0188901 A1 | 8/2008 | Sanghera et al. |
| 2008/0215110 A1 | 9/2008 | Gunderson |
| 2008/0221632 A1 | 9/2008 | Bardy et al. |
| 2008/0228093 A1 | 9/2008 | Dong et al. |
| 2008/0243200 A1 | 10/2008 | Scinicariello et al. |
| 2008/0262559 A1 | 10/2008 | Zhang et al. |
| 2008/0275516 A1 | 11/2008 | Ghanem et al. |
| 2008/0275517 A1 | 11/2008 | Ghanem et al. |
| 2008/0275519 A1 | 11/2008 | Ghanem et al. |
| 2008/0275521 A1 | 11/2008 | Warren et al. |
| 2008/0288009 A1 | 11/2008 | Kim et al. |
| 2009/0036788 A1 | 2/2009 | Nabutovsky et al. |
| 2009/0043352 A1 | 2/2009 | Brooke et al. |
| 2009/0054796 A1 | 2/2009 | Sanghera et al. |
| 2009/0054938 A1 | 2/2009 | Ostroff et al. |
| 2009/0093731 A1 | 4/2009 | Palreddy et al. |
| 2009/0156957 A1 | 6/2009 | Linder et al. |
| 2009/0157128 A1 | 6/2009 | Seim et al. |
| 2009/0157132 A1 | 6/2009 | Linder et al. |
| 2009/0157137 A1 | 6/2009 | Gilkerson et al. |
| 2009/0187227 A1 | 7/2009 | Palreddy et al. |
| 2009/0228057 A1 | 9/2009 | Allavatam et al. |
| 2009/0240157 A1 | 9/2009 | Lian et al. |
| 2009/0240300 A1 | 9/2009 | Lian et al. |
| 2009/0259271 A1* | 10/2009 | Allavatam .......... A61B 5/0452 607/25 |
| 2010/0004713 A1 | 1/2010 | Warren et al. |
| 2010/0094369 A1 | 4/2010 | Allavatam et al. |
| 2010/0152798 A1 | 6/2010 | Sanghera et al. |
| 2010/0152799 A1 | 6/2010 | Sanghera et al. |
| 2010/0185109 A1 | 7/2010 | Zhang et al. |
| 2010/0331904 A1 | 12/2010 | Warren et al. |
| 2011/0098585 A1 | 4/2011 | Warren et al. |
| 2011/0098775 A1 | 4/2011 | Allavatam et al. |
| 2012/0046563 A1 | 2/2012 | Allavatam et al. |
| 2013/0006085 A1 | 1/2013 | Allavatam et al. |

FOREIGN PATENT DOCUMENTS

| | | |
|---|---|---|
| CN | 1915166 A | 2/2007 |
| CN | 1985750 A | 6/2007 |
| CN | 101065059 A | 10/2007 |
| EP | 0554208 A2 | 8/1993 |
| EP | 1774907 A1 | 4/2007 |
| EP | 2313153 B1 | 4/2012 |
| EP | 2455132 A1 | 5/2012 |
| JP | 2006523505 A | 10/2006 |
| JP | 2007501099 A | 1/2007 |
| JP | 2007510447 A | 4/2007 |
| JP | 2008536633 A | 9/2008 |
| JP | 2013248530 A | 12/2013 |
| WO | 2004105871 A1 | 12/2004 |
| WO | 2009111764 A2 | 9/2009 |
| WO | 2009111766 A2 | 9/2009 |
| WO | 2009137726 A2 | 11/2009 |

OTHER PUBLICATIONS

Olson et al. "Onset and Stability for Ventricular Tachyarrhythmia Detection in an Implantable Pacer-Cardioverter-Defibrillator," IEEE, pp. 167-170, 1987.

(56) References Cited

OTHER PUBLICATIONS

"QT Interval," Wikipedia, [Online]. Retrieved from the Internet: <URL: http://en.wikipedia.org/wiki/QT_interval>, (Accessed May 11, 2011), 5 pgs.
Schuder, "The Role of an Engineering Oriented Medical Research Group in Developing Improved Methods and Devices for Achieving Ventricular Defibrillation: The University of Missouri Experience." PACE, vol. 16, pp. 95-124, Jan. 1993.
Schwake et al., "Komplikationen nit Sonden bei 340 Patienten mit einem Implantierbaren Kardioverter/Defibrillator." Z Kardiol, 88:8, pp. 559-565, 1999.
Swerdlow et al., "Advanced ICD Troubleshooting: Part I." PACE, vol. 28, [Online]. Retrieved from the Internet: <http://www.medscape.com/viewarticle/520588_print>, pp. 1322-1346, Jan. 9, 2006.
Throne et al., "A Comparison of Four New Time-Domain Techniques for Discriminating Monomorphic Ventricular Tachycardia from Sinus Rhythm Using Ventricular Waveform Morphology." IEEE Transactions on Biomedical Engineering, vol. 38(6), pp. 561-570, Jun. 1991.
Von Dem Wildenberg et al., "Biotransformation of trans-5-chloro-2-methyl-2,3,3a,12b-tetrahydro-1-H-dibenz [2,3:6,7]oxepin o [4,5-c]pyrrolidine maleate in rats," Arzneimittelforschung, vol. 40(5), pp. 540-544, May 1990.

\* cited by examiner

USE OF DETECTION PROFILES IN AN IMPLANTABLE MEDICAL DEVICE

CROSS REFERENCE TO RELATED APPLICATIONS

The present application is a continuation of U.S. application Ser. No. 14/815,267, filed Jul. 31, 2015, which claims the benefit of and priority to U.S. Provisional Application No. 62/037,288, filed on Aug. 14, 2014, the disclosure of which is incorporated herein by reference.

BACKGROUND

Implantable cardiac monitoring and/or stimulus systems are often designed to detect individual cardiac cycles or "beats." It is common to design these systems to identify the R-wave or QRS complex of the cardiac signal. The R-wave or QRS complex can often be distinguished by virtue of being the largest amplitude signal. A "detection profile" can be used to detect events. Some illustrative examples of R-wave or QRS complex detection are shown in U.S. Pat. No. 5,709,215 to Perttu et al., and U.S. Pat. No. 8,565,878 to Allavatam et al., the disclosures of which are incorporated herein by reference.

Various difficulties with detection can arise, including variations in amplitude from one beat to the next and poor signal to noise ratio. These issues can cause overdetection of the cardiac signal, as may happen if both the R-wave and T-wave of a single cardiac cycle are incorrectly identified as being both R-waves of two separate cardiac cycles.

OVERVIEW

The present inventor has recognized that in some instances a detection profile may avoid overdetection with a "close call." In such cases, the present invention, in an illustrative embodiment, is designed to identify the close call and modify the manner in which at least one subsequent cardiac event is detected.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Each of the following non-limiting examples can stand on its own, or can be combined in various permutations or combinations with one or more of the other examples.

As used herein, a signal is sensed by an implantable cardiac device system, events are detected in the sensed signal, and cardiac rhythms are classified by use of the detected events. Detected events may also be referred to as detections. Classification of the cardiac rhythms may be referred to as rhythm analysis. Cardiac rhythm classification can include identification of malignant conditions, such as ventricular fibrillation or certain tachyarrhythmias, for example.

The present invention may be used in implantable monitoring or therapy systems. Implantable therapy systems make therapy/stimulus decisions in reliance upon rhythm classification, while monitoring systems make data recording decisions using rhythm classification, where applicable. Therapy systems may deliver electrical, pharmaceutical or other therapy. Some illustrative implementations of the present invention may be in pacemakers and defibrillators, though other implementations are also envisioned. Any of these systems can, if so configured and enabled, generate annunciating (audible tones or palpable vibrations) or communicating (telemetry) signals in response to rhythm classification, in addition to or as an alternative to therapy. Implantable monitoring systems may use cardiac signal analysis to determine whether data is to be recorded for later retrieval, or to take other actions such as emitting a warning or annunciating data.

Figure 1:
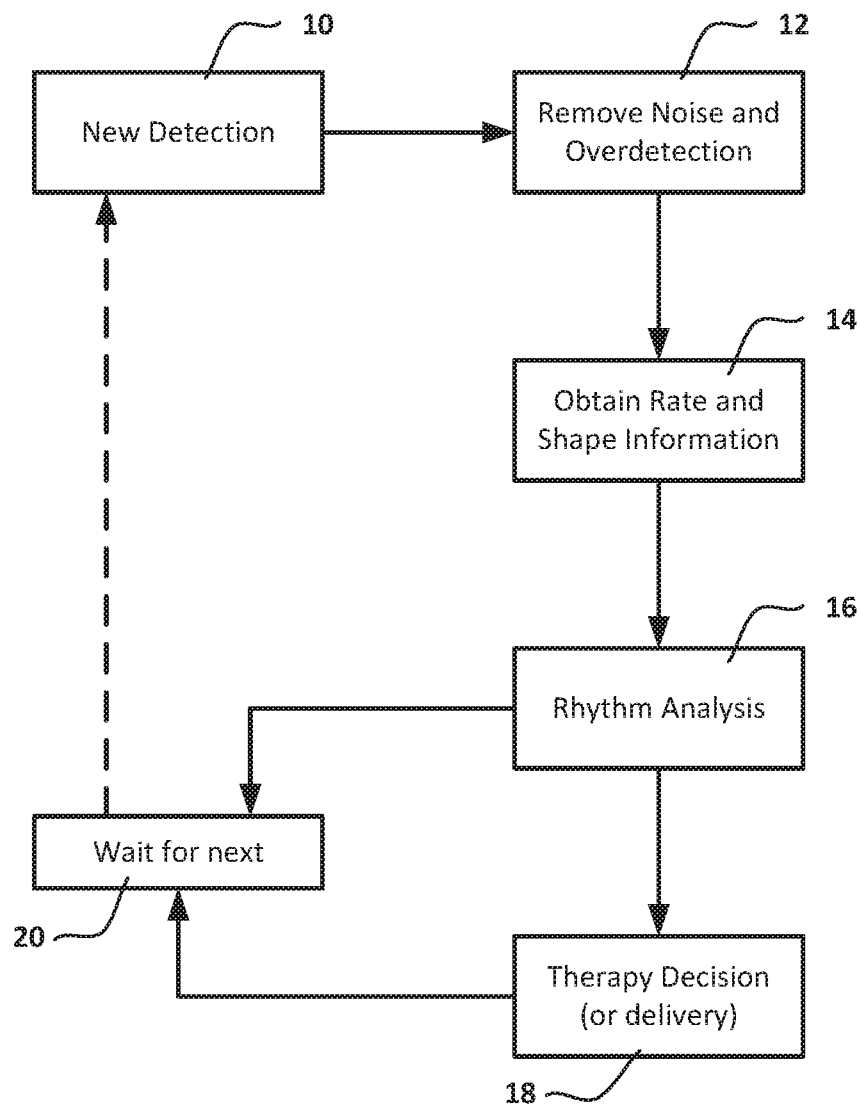
FIG. 1 shows an overall method of cardiac signal analysis including rhythm analysis and therapy decisions.

FIG. 1 shows, in block form, a method of cardiac signal analysis for an implantable medical device. The analysis is cyclic and can be understood as beginning with a new detection or detected event 10. Illustrative detection methods are shown below and may be understood from U.S. Pat. No. 5,709,215, titled R-WAVE DETECTION METHOD FOR IMPLANTABLE CARDIOVERTER DEFIBRILLATORS, and U.S. Pat. No. 8,565,878, titled ACCURATE CARDIAC EVENT DETECTION IN AN IMPLANTABLE CARDIAC STIMULUS DEVICE, the disclosures of which is incorporated herein by reference. Other detection methods may be used instead.

Once a detected event is identified, the analysis then performs assessments to identify noise and/or overdetection as shown at 12. Noise may be identified, for example, as shown in U.S. Pat. No. 8,744,555, titled ADAPTIVE WAVEFORM APPRAISAL IN AN IMPLANTABLE CARDIAC SYSTEM, the disclosure of which is incorporated herein by reference. Overdetection may be identified, for example, as shown in U.S. Pat. Nos. 8,160,686 and 8,160,687, each titled METHODS AND DEVICES FOR ACCURATELY CLASSIFYING CARDIAC ACTIVITY, U.S. Pat. No. 8,265,737, titled METHODS AND DEVICES FOR IDENTIFYING OVERDETECTION OF CARDIAC SIGNALS, and/or US Published Patent Application No. 2012-0046563, titled METHODS AND DEVICES THAT IDENTIFY OVERDETECTION IN IMPLANTABLE CARDIAC SYSTEMS, the disclosures of which are incorporated herein by reference. Other noise identification and/or overdetection identification methods may be used instead to address malsensing and enhance the accuracy of counting of cardiac cycles.

Next, the analysis method obtains certain useful data such as rate and shape information, as shown at 14. Rate and shape information may then be used for rhythm analysis 16. If the rhythm analysis at 16 determines that therapy may be needed, a therapy decision can be made, as shown at 18. The analysis then waits for the next new detection, as shown at 20.

Illustrative methods useful in blocks 14, 16 and/or 18 are shown in the above incorporated patents and published patent applications as well as U.S. Pat. No. 6,754,528, titled APPARATUS AND METHOD OF ARRHYTHMIA DETECTION IN A SUBCUTANEOUS IMPLANTABLE CARDIOVERTER/DEFIBRILLATOR, U.S. Pat. No. 7,330,757, titled METHOD FOR DISCRIMINATING BETWEEN VENTRICULAR AND SUPRAVENTRICULAR ARRHYTHMIAS, US Published Patent Application No. 2010-0331904, titled ADAPTIVE CONFIRMATION OF TREATABLE ARRHYTHMIA IN IMPLANTABLE CARDIAC STIMULUS DEVICES, and U.S. Pat. No. 8,588,895, titled ROBUST RATE CALCULATION IN AN IMPLANTABLE CARDIAC STIMULUS OR MONITORING DEVICE, the disclosures of which are each incorporated herein by reference. In addition to these patents and patent applications, various methods are known in the art from various commercially available implementations.

Figure 2:
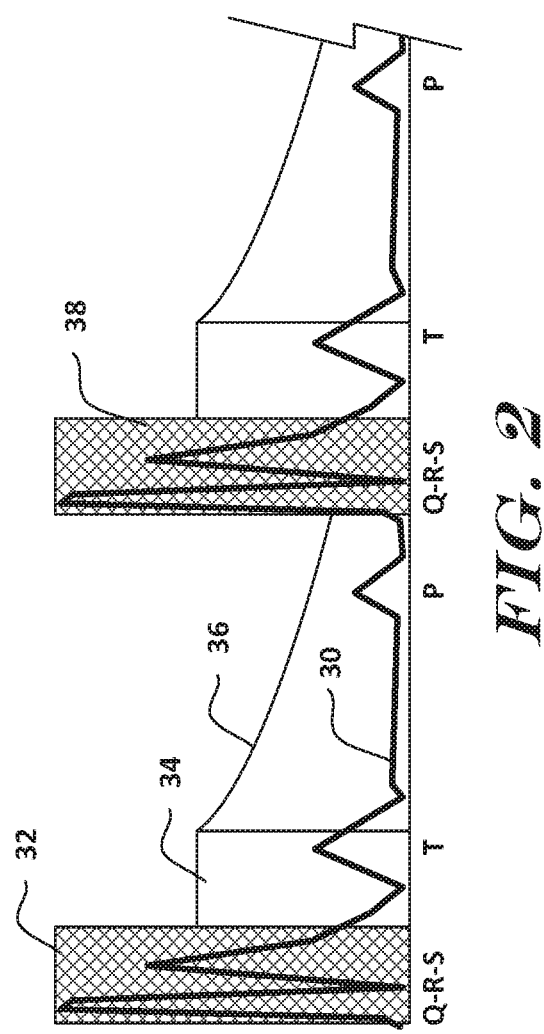
FIG. 2 illustrates the application of a detection threshold using a detection profile to a cardiac signal.

FIG. 2 illustrates the application of a detection threshold to cardiac signals for both normal and treatable high rate cardiac rhythms. A cardiac cycle typically includes several portions (often referenced as "waves") which, according to well-known convention, are labeled with letters including P, Q, R, S, and T, each corresponding to certain physiological events. A normal cardiac cycle usually has all of these parts, though not all may be visible on any given cardiac signal representation. Certain components may not be visible due to factors such as elevated rate, choice of sensing vector, anatomic anomaly, or active arrhythmia, for example. The combination of Q, R and S "waves" can be referred to as the QRS complex. The R-wave and/or QRS complex is often the component of the cardiac cycle that is detected for purposes of identifying a cardiac cycle, since it is typically the largest amplitude component. In some examples, other components may be the target for detection instead, such as the atrial depolarization or P-wave.

In FIG. 2, a cardiac signal is shown at 30, with indications of the Q, R, S, T and P waves shown below. An illustrative detection threshold is shown including a refractory period 32, a constant threshold period 34 and a decay period 36. The refractory period 32 defines a time during which the system's operational circuitry will not detect an event, while the constant threshold period and decay period collectively define a time period during which the system's operational circuitry will detect an event if the sensed signal 30 crosses one of lines 34 or 36.

The detection threshold 32/34/36 relies in part on the "estimated peak" of the QRS complex, as well as a detection profile. The estimated peak is a measure of amplitude or magnitude, depending on the particulars of a given embodiment, of the cardiac signal being monitored. As the signal grows larger, so too does the estimated peak. In some examples, an estimated peak is the largest peak in a given QRS complex. In other examples, the estimated peak is an average of the largest peaks in the previous two detected cardiac events. Other measures, averages or the like may be used. The estimated peak may be used, for example, by setting the amplitude for the constant threshold period 34 at a percentage of the estimated peak, and/or by setting the beginning point of the decay period 36 to a fraction of the estimated peak.

Figure 3:
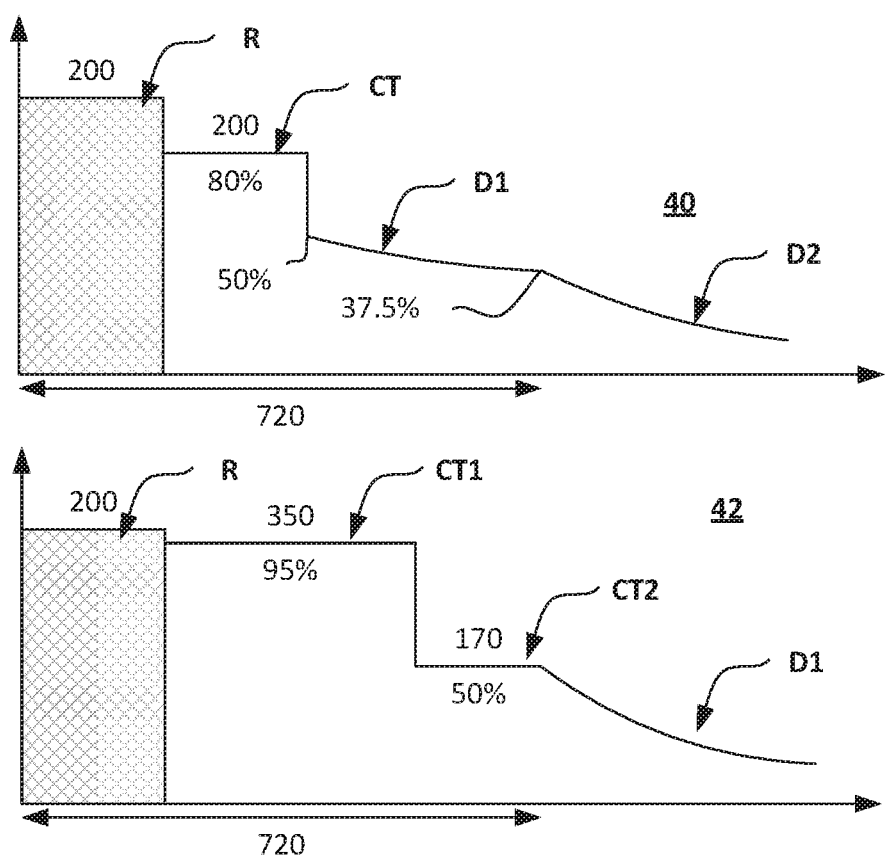
FIG. 3 illustrates multiple detection profiles that can be used in an implantable system in response to different inputs and conditions.

The detection threshold is also defined by a detection profile, which defines the durations, slopes and percentages used to calculate the threshold for application to a particular cardiac signal. Illustrative detection profiles are shown in FIG. 3. A first detection profile is shown at 40. The detection profile 40 includes a refractory period, R, a constant threshold period, CT, a first decay period D1, and a second decay period D2. In profile 40, the refractory period R illustratively has a duration of 200 milliseconds, during which additional detections cannot occur.

The constant threshold period allows additional events to be detected if the cardiac signal crosses a constant threshold set to a percentage of the estimated peak. In the example, detection profile 40 applies a constant threshold, CT, of 80% of the estimated peak for a period of 200 milliseconds after the refractory period. Next, the first decay D1 of detection profile 40 has an initial threshold at 50% of the estimated peak and decays over time to an ending threshold of 37.5% of the estimated peak. The first decay D1 lasts 320 milliseconds, such that the total time to the start of the second decay D2 is 720 milliseconds. The second decay starts at 37.5% of the estimated peak and decays to a predetermined, fixed noise floor for the system. The decay periods D1, D2 of detection profile 40 illustratively use a decay constant of 400 milliseconds. Other time constants can be used instead.

A second detection profile is shown at 42. Here, detection profile 42 has the same refractory period R, with a duration of 200 milliseconds. The second detection profile 42 is less sensitive to cardiac signals than the first detection profile 40 because, at least, the constant threshold period CT1 after the refractory period has a higher threshold (95% of estimated peak, rather than 80%), and a longer duration at the higher threshold (350 milliseconds before dropping, rather than 200 milliseconds). Another example of the second detection profile 42 being less sensitive than the first detection profile 40 can be noted as decay period D1 of profile 40 is replaced with a constant threshold period CT2, beginning and ending at 50% of the estimated peak, rather than beginning at 50% and decaying to 37.5%. Finally, the second detection profile 42 is also less sensitive to cardiac signals than the first detection profile 40 because the decay period, D1 of detection profile 42, starts at 50% of the estimated peak and goes to the noise floor, while the late decay period D2 of detection profile 40 starts at 37.5% of the estimated peak instead.

The specifics of the detection profiles 40, 42 are merely illustrative of one approach and can be varied widely. Additional profiles may be provided as well, for example as shown in U.S. Pat. No. 8,565,878. Pertinent to the present invention is that multiple detection profiles are available. In some examples, a single "profile" that has multiple variants, such as multiple ways to calculate estimated peak, or a single change of one of the parameters, can be considered multiple profiles.

Returning to FIG. 2, accurate detection of the QRS complex occurs, as the refractory period 32 lasts long enough to cover the entire QRS complex, and the combined constant threshold period 34 and decay period 36 pass over the T-wave and P-wave without an additional detection occurring. That the detection is accurate is observed by noting that there is one refractory period 32, 38, shown in the cross hatching, for each QRS complex.

Figure 4:
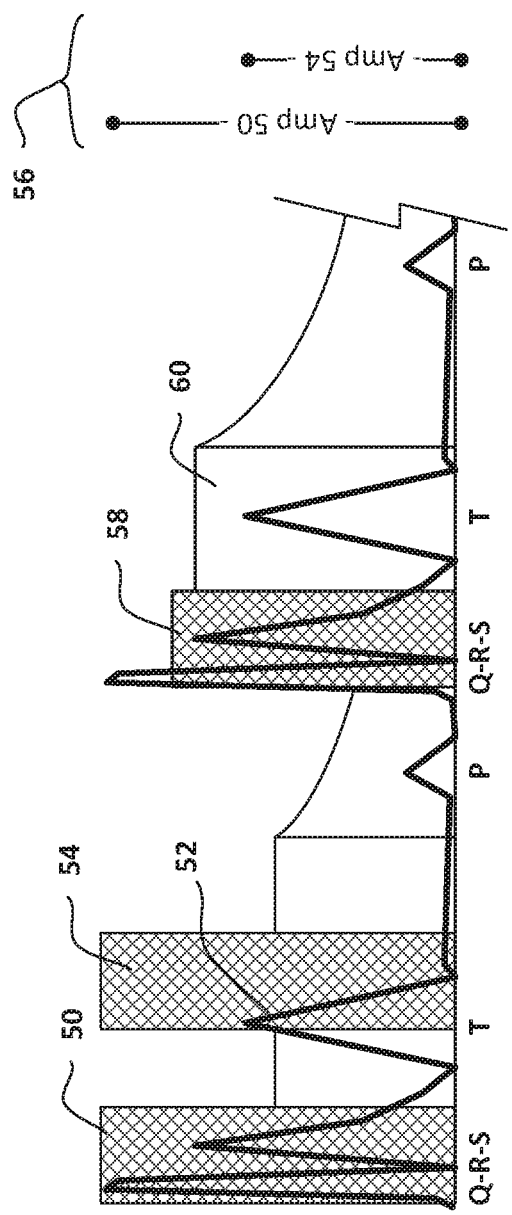
FIG. 4 shows a modification to a detection profile, and its effect on detection thresholds, in view of dis-similarities between previously detected events.

FIG. 4 shows a modification to a detection profile, and its effect on detection thresholds, in view of dis-similarities between previously detected events. A first refractory period is illustrated at 50, covering a QRS complex. However, a large T-wave follows at 52, causing a second detection indicated by the second refractory period 54. In this example, an amplitude analysis is performed as shown at 56, comparing the peak amplitude during the refractory period 50 with the peak amplitude during refractory period 54. Because the two amplitudes are different, as shown at 56, the system is configured to select a different detection profile for use after detected event 58.

It should be noted that in FIG. 4 (as well as the other figures herein), the height of the cross-hatched refractory period 50, 54, 58 is representative of the calculated "estimated peak", on which the detection threshold is based along with the detection profile. In the example of FIG. 4, the estimated peak is identified using one or more previously detected events, such that the estimated peak for refractory period 54 is based on the peak amplitude during refractory period 50, averaged with the amplitude peak during refractory of an immediately preceding refractory period (not shown). For detection 58, the estimated peak is the average of the peak amplitude during refractory 50 and the peak amplitude during refractory 54, yielding a lower estimated peak than the amplitude during refractory period 58.

Here, the detection thresholds applied after refractory periods 50, 54 are based on detection profile 40 in FIG. 3. The detection threshold after refractory period 58, however, is based on detection profile 42 from FIG. 3. As a result, the constant threshold period 60 passes easily over the T-wave, avoiding repeated overdetection. A similar approach to cardiac event detection is shown in U.S. Pat. No. 8,565,878.

Figure 5:
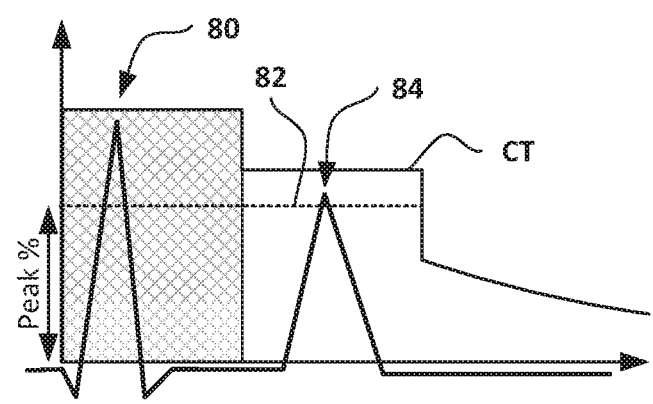
FIG. 5 illustrates a method of identifying a "close call"

The present invention expands on the concept shown in FIG. 4 by including a "close call" analysis, so that an extra detection is not required to take place in order to have the less sensitive detection profile called. FIG. 5 illustrates a method of identifying a "close call". A cardiac signal is shown relative to a detection threshold having a refractory period 80. A threshold for "close call" is defined at 82, using a percentage of the estimated peak in this example. This threshold sits below the detection threshold, and is only applied, in this example, for a limited duration following the refractory period 80. In the example, shown the close call threshold applies during the constant threshold period CT. In the illustrative example, the close call threshold is determined at 45% of the estimated peak, where the CT threshold is 50% of the estimated peak. In other examples, the close call threshold may be in the range of 40% to 48% of the estimated peak. In another example, the close call threshold is set as a percentage of the detection threshold in the range of 70-95% thereof.

A cardiac signal that crosses the detection threshold, in various examples, would not be deemed a close call, since it actually caused a detected event to be identified. Signals that cross the ordinary detection threshold may be analyzed as shown in FIG. 4.

In some examples, meeting the close call amplitude threshold is sufficient to declare a close call. In other examples, the close call amplitude threshold is but one of two or more rules to be met, as further illustrated in FIG. 6. The various versions of second, or third or more rules, that are shown in FIG. 6 may be combined together and included as part of a confirmation step.

Figure 6:
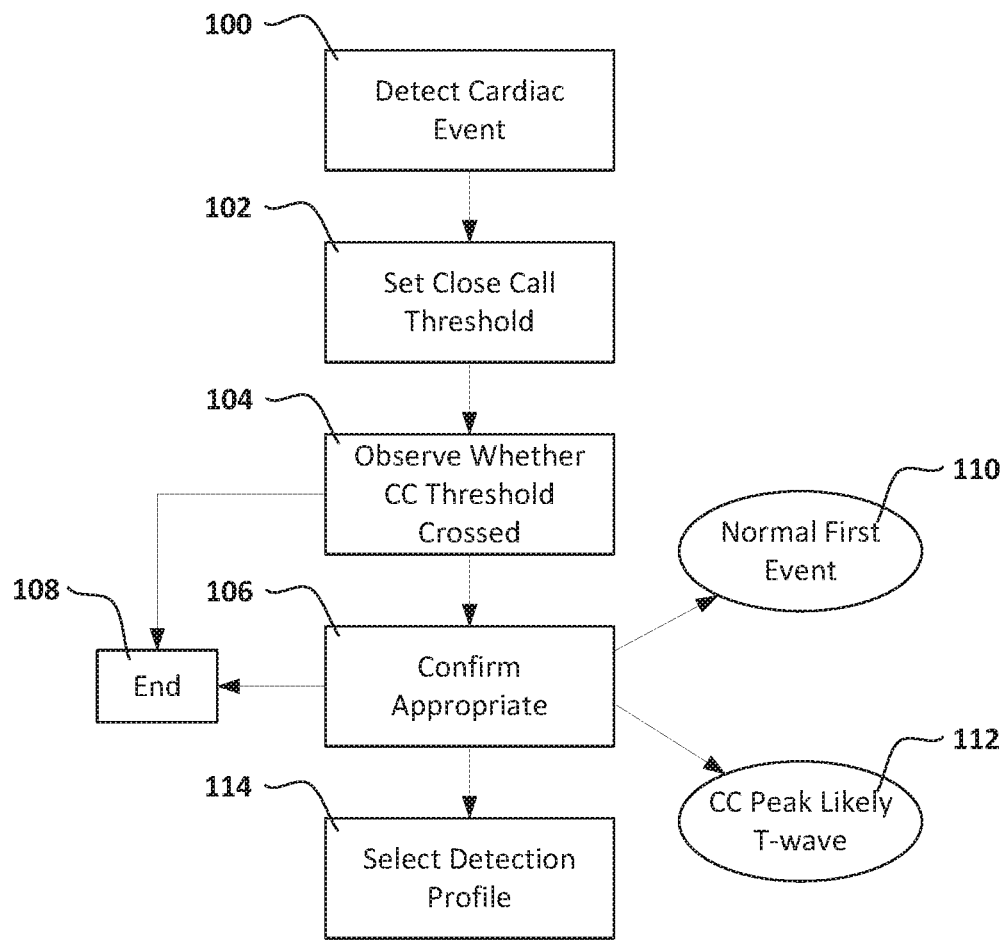
FIG. 6 illustrates the analysis of FIG. 5 in a block form.

FIG. 6 illustrates the analysis of FIG. 5 in a block form, with additional details. The method as shown may be performed by the device operational circuitry. Illustrative operational circuitry can include a microprocessor or microcontroller, with associated memory and logic circuits for storing data and performing analytical or filtering functions, for example, as well as amplifiers and other filtering circuits and switches to allow the selection and preprocessing of an incoming cardiac signal from implantable electrodes. Analog-to-digital circuitry is typically provided, along with various other elements further detailed below.

Starting with the detection of a cardiac event 100, the method sets a close call threshold 102. As noted above, the close call threshold may be determined as a percentage or other function of an estimated peak or of the detection threshold to be applied to the incoming cardiac signal. The method determines whether the close call threshold is determined at 104. If the close call threshold is crossed at 104, the method next confirms that a close call determination is appropriate, as shown at 106. If the close call threshold is not crossed, or if a close call determination is deemed not appropriate, the method ends at 108.

Regarding appropriateness, there are a plurality of double checks that may be performed. More than one of these double checks may be combined together. As a first matter, however, the confirmation step 106 is optional and/or omitted in some embodiments. In other embodiments, confirmation 106 includes determining that the event preceding the close call threshold crossing is "normal", as shown at 110. Such measures of whether the preceding event is "normal" can be combined together or used separately.

Measures of normality 110 can include determining if the preceding ("first") cardiac event is narrower than a width threshold. The width threshold may be set as desired; for near field sensing (i.e. with two electrodes inside the heart of the patient, or at least one electrode on the patient's heart), a width in the range of 40-100 milliseconds may be appropriate; for far field sensing (i.e. with two spaced electrodes not inside of or in contact with the heart), a width in the range of 60-150 milliseconds may be more appropriate. In an example, a subcutaneous-only system using widely spaced electrodes sets a normal width using a fixed threshold of 100 milliseconds. In another example, a subcutaneous-only system is configured to calculate a normal sinus rhythm template and measure the width thereof, with a width threshold set to be slightly larger than the width of the template, for example by adding 10-20 milliseconds to the template width. Examples of template formation can be found in U.S. Pat. No. 7,376,458, titled METHOD FOR DEFINING SIGNAL TEMPLATES IN IMPLANTABLE CARDIAC DEVICES, the disclosure of which is incorporated herein by reference.

Another measure of normality can be determined by comparing the preceding detected event that occurred before the close call threshold crossing to a template. Examples of template comparison can be found in U.S. Pat. No. 7,477,935, titled METHOD AND APPARATUS FOR BEAT ALIGNMENT AND COMPARISON, and U.S. Pat. No. 8,160,687, titled METHODS AND DEVICES FOR ACCURATELY CLASSIFYING CARDIAC ACTIVITY, the disclosure of which is incorporated herein by reference. Templates can be stored, static templates, or may be dynamic templates which change over time or which each newly detected event/beat.

Another way to confirm whether it is appropriate to declare a close call is to determine whether the peak causing the close call threshold crossing is likely to be a T-wave, as shown at 112. In one example, such confirmation is performed by applying a known formula for determining a QT interval. Examples include:

Bazett's formula:

$$QT(Exp)=QT*\sqrt{RR}$$

Fridericia's formula:

$$QT(\text{Exp}) = QT * \sqrt[3]{RR}$$

And the Sagie et al. regression formula:

$$QT(Exp)=QT+A*(RR-1)$$

Sagie et al. found A=0.154. In these formulas, "RR" stands for the interval between two R-waves, and QT stands for the interval from the Q wave peak, starting the QRS complex, to the T-wave peak in a given cardiac cycle.

In another example, finding that the close call threshold was crossed by a likely T-wave may be determined by confirming that the width of the peak that causes the close call is greater than the width of the preceding detected cardiac event by some margin. For example, the peak associated with the close call threshold crossing would have to be at least 40 milliseconds wider than the preceding detected cardiac event.

In certain examples, two or more confirmation criteria are combined, for example, a combination of the "close call" being wider than the preceding detected event and occurring at an expected time as determined by one of the above formulas for predicting QT interval. Other combinations of any of these criteria may be used in additional alternative examples.

If the confirmation step 106 is passed, the method then modifies the selection of detection profile. In an example, a detection profile is selected for use in the next "N" detected events which is less sensitive than one or more other detection profiles. For example, profile 42 in FIG. 3 would be selected over profile 40 of FIG. 3. N may be any number, for example in a range of 1-8 detected events. In some examples, N=1.

Figure 7:
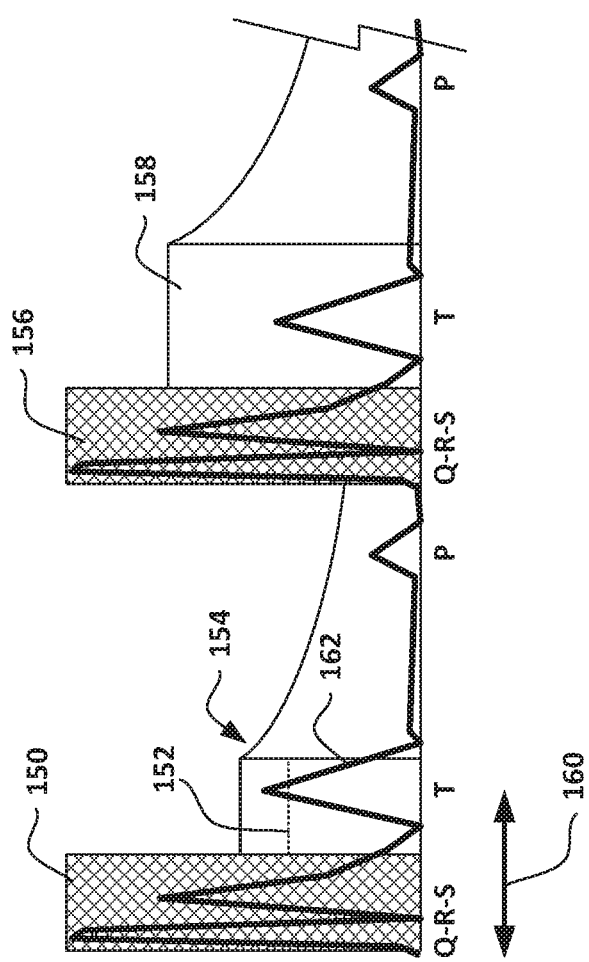
FIG. 7 shows the method of FIG. 6 as operated on an example cardiac signal.

FIG. 7 shows the method of FIG. 6 as operated on an example cardiac signal. A first detected event is associated with the refractory period 150. A close call detection threshold is set as shown at 152, below the detection profile and only operative, in this example, during an initial constant threshold period. As shown at 154, the cardiac signal crosses the close call detection threshold 152. In response thereto, following the next detected event at 156, a different detection profile is applied. As shown at 158, the newly selected detection profile sits well above the T-wave for the second detection and is less sensitive to the cardiac signal.

As noted in FIG. 6, some secondary factors may be considered to confirm the close call threshold crossing is suitable or appropriate for applying the less sensitive detection profile. For example, the interval 160 may be analyzed using an accepted formula, the width of event 162 may be analyzed, the width of the R-wave in the QRS complex may be analyzed, or the template match of the QRS complex to a template may be assessed.

Figure 8:
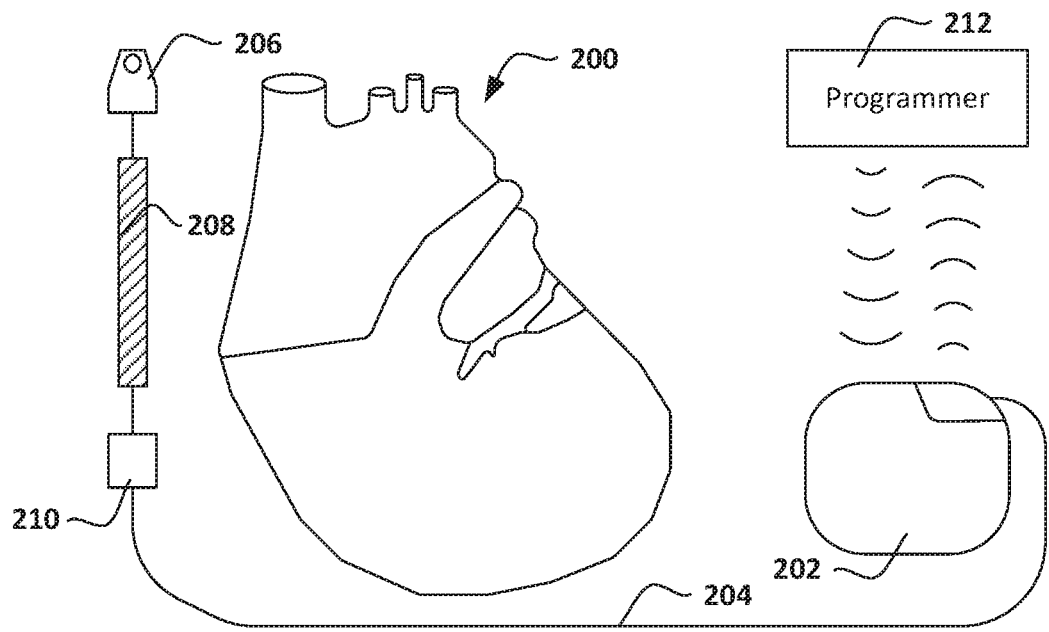
FIGS. 8-9 show illustrative subcutaneous-only and transvenous, intracardiac rhythm management systems, respectively.
Figure 9:
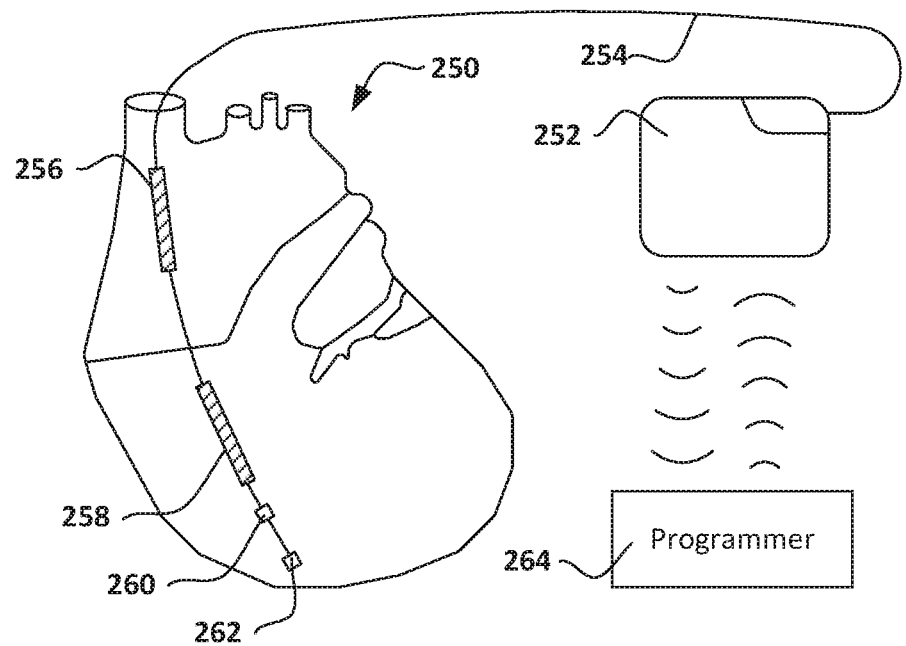

The present invention may find application in a subcutaneous-only system as illustrated in FIG. 8, or in a transvenous system as shown in FIG. 9. Alternatives may include systems having multiple subcutaneous and transvenous elements, epicardial systems, or fully intravenous or intracardiac systems.

The illustrative system shown in FIG. 8 is shown relative to a heart 200 and is intended to convey a subcutaneous implant that would take place over the ribs of the patient and beneath the patient's skin. A canister 202 is implanted near the left axilla, with lateral, anterior, or posterior positions being possible. A lead 204 couples the canister 202 to electrodes 206, 208 and 210, which are illustrated as implanted along the sternum of the patient, typically to the left or right thereof. The system in FIG. 8 may include an external programmer 212 configured for communication with the implant 202.

The system in FIG. 9 is a transvenous system, illustratively shown relative to the heart 250 again with the patient's ribs omitted for clarity. The canister 252 is in a high pectoral position, with the lead 254 accessing the vasculature and entering the heart. The lead 254 may include a superior vena cava coil electrode 256, a right ventricular coil electrode 258, and one or two ventricular sense/pace electrodes 260, 262. Again a programmer is shown at 264 and configured for communication with the implanted system. The system may further include a left ventricular lead (not shown).

Communication for either of the systems in FIG. 8 or 9 may be inductive, RF or via any other suitable medium of communication. Such communication can be useful to configure the implanted system for sensing, therapy or other feature, to load new software or firmware for the implanted system, and to retrieve information about system operation such as device status, therapy history, diagnostic data (both device and patient related), or other suitable data. The programmers may contain such circuitry as is needed to provide processing, memory, display, telemetry/RF communications and the like for these noted purposes.

The canisters in FIGS. 8 and 9 contain operational circuitry for the implantable system. The operational circuitry may include a controller and any suitable analog and/or digital circuits needed for signal processing, memory storage and generation of high-power electrical, low-power electrical and/or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes. The leads and external shell for the canisters can be manufactured with various materials suitable for implantation, such as those widely known, along with coatings for such materials, throughout the art. For example, the canisters can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes can be formed of suitable materials as well, such as silver, gold, titanium or stainless steel such as MP35N stainless steel alloy, or other materials.

The location of system implant may vary. For example, the system shown is a subcutaneous-only system located on the anterior and lateral chest between the skin and ribcage of the patient. Other subcutaneous only systems (including systems without a lead 204, with multiple leads 204, or an array in place of lead 204) may be used with other anterior only placements and/or anterior-posterior, posterior only, left-right, etc. locations, including, for example, locations noted in U.S. Pat. Nos. 6,647,292, 6,721,597, 7,149,575, 7,194,302, each of which is incorporated herein by reference, and other locations as well. Subcutaneous placement can include any location between the skin and ribcage, including sub-muscular. A subcutaneous-only defibrillator may also be used in combination with a fully intracardiac device such as a seed pacer, for example, the Nanostim™ leadless pacemaker or Micra™ transcatheter pacing system.

Other systems may include one or more transvenous leads or epicardial leads/electrodes, and may use different canister implant locations, such as placing the canister in a higher pectoral position closer to the clavicle for closer venous access, or abdominal placement. Illustrative transvenous systems include single chamber, dual chamber and biventricular systems. A fully intravenous system has also been proposed. Additional or other coatings or materials than those noted above may be used, particularly for epicardial, transvenous or intravenous systems, leads and canisters.

Various alternatives and details for these designs, materials and implantation approaches are known to those skilled in the art. Commercially available systems in which the above methods can be performed or which may be configured to perform such methods are known including the Boston Scientific Teligen™ ICD and S-ICD™ System, Medtronic Concerto™ and Virtuoso™ systems, and St. Jude Medical Promote™ RF and Current™ RF systems. Such platforms include numerous examples and alternatives for the operational circuitry, battery, canister, lead, and other system elements.

Figure 10:
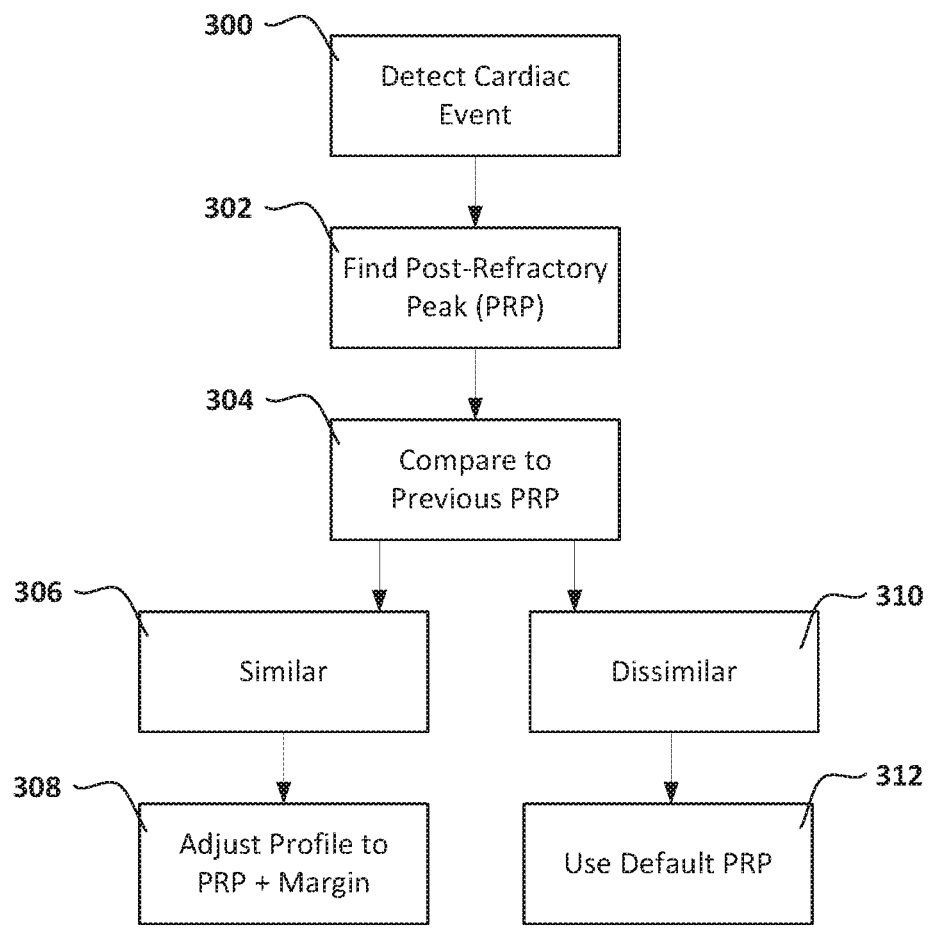
FIG. 10 shows another illustrative method in block flow format.

Yet another illustrative method is shown in the block diagram of FIG. 10. Here, the detection profile automatically adjusts to the signal which is not detected—that is, the peak occurring during a post-refractory period which fails to cross the detection threshold, rather than adjusting to the R-wave signal itself. In this example, the method begins with detection of a cardiac event, as shown at 300. Next, using a detection profile which has a refractory period plus a following detection period, a post-refractory peak (PRP) is identified, as shown at 302. A particular period may be set for the PRP (the PRP period), with a set duration. For example, the PRP period may be the constant threshold period 34 as shown in FIG. 2. Illustrative durations for the PRP period may be in the range of 100 to 300 milliseconds. The PRP period may be set as shown by FIG. 2, based upon the time of the detection threshold crossing. In other examples, the PRP period can be set according to a window after the R-wave peak during refractory, in the range of, for example, 200 to 350 milliseconds after the R-wave peak (that is, a 150 millisecond window staring 200 milliseconds after the R-wave peak).

Next, as shown at 304, the PRP is (optionally) compared to a previous PRP, or an average of several previous PRPs. This step 304 may be useful to ensure that the adjustments performed in block 308 are only performed if the detected signal is relatively consistent in its amplitude components. Thus, if the PRP is similar to previous PRP value(s), as indicated at 306, then the detection profile for use in the next cardiac cycle is adjusted to use the PRP plus a margin, as shown at 308, during the window for PRP detection.

Thus, referring to FIG. 2, again, the duration during the constant threshold period 34 would the set to the maximum signal peak plus some margin. The margin may be set in the digital domain using, for example, 5 to 10 ADC counts. In another example, the margin is set in the analog domain using, for example, 50 to 150 microvolts for an R-wave signal having maximum amplitude between 500 microvolts and 2 millivolts. The margin may be adaptive to the detected R-wave peak and set, for example, as a percentage (5-20%) thereof.

Going back through the drawing, if the PRP is not similar to the prior PRP value(s), then the dissimilar path 310 is followed, and an ordinary detection threshold setup, as described in other patents and noted above, may be used, as shown at 312. As noted previously, block 304 may be bypassed, if desired, such that the method simply jumps to block 308. Alternative, some other "stable signal" rule can be used, for example looking at R-wave peaks themselves rather than the signal in a PRP window to determine similarity.

VARIOUS NOTES & EXAMPLES

A first non-limiting example takes the form of an implantable cardiac system including a plurality of electrodes coupled to operational circuitry configured to analyze cardiac signals, the system comprising detecting means for detecting a first cardiac event by the application of a detection profile which defines a detection threshold, the detecting means configured to use at least first and second detection profiles, with the second detection profile having lesser sensitivity to cardiac signals than the first detection profile. Examples of detecting means are shown by FIG. 6 at 100 and associated text.

The first non-limiting example is characterized in that the system further includes close call means for determining whether a close call has occurred in which the cardiac signal nearly caused a likely overdetection but did not, the close call means adapted to set a close call threshold relative to the detection threshold and determining whether a cardiac signal associated with the first cardiac event crosses the close call threshold without crossing the detection threshold following the first cardiac event. The close call means is illustrated in FIG. 6 including means to set a threshold 102 and observe whether the threshold is crossed 104, as well as associated text. Further in the first non-limiting example, the detecting means is configured to respond to the close call means such that, if the close call means determines a close call has occurred after the first cardiac event, the detecting means will select the second detection profile rather than the first detection profile for detecting at least one subsequent cardiac event. Such a responsive element is illustrated in FIG. 6 with the selection of the detection profile at 114 and associated text.

A second non-limiting example takes the form of a system as in the first non-limiting example, wherein: the detection means is configured to detect a second cardiac event following the first cardiac event; the close call means is configured to analyze the time period between the first cardiac event and the second cardiac event to determine whether a close call has occurred and, if so, the detection means is configured to respond to the close call means by selecting the second detection profile for use after the second cardiac event is detected until at least a third cardiac event has taken place.

A third non-limiting example takes the form of a system as in either the first or second non-limiting examples, wherein the close call means comprises confirmation means to confirm that it is appropriate to declare a close call if the close call threshold is crossed at a time, relative to the first cardiac event, when it is likely that a T-wave would occur. A fourth non-limiting example takes the form of a system as in the third non-limiting example, wherein the confirmation means is configured to use an accepted formula for determining a QT Interval to determine whether the close call threshold is crossed at a time when it is likely that a T-wave could occur. A fifth non-limiting example takes the form of a system as in the fourth non-limiting example, wherein the accepted formula is one of Fridericia's formula, Bazett's formula, or the Sagie et al. regression formula.

A sixth non-limiting example takes the form of a system as in the third non-limiting example, wherein the confirmation means further comprises means to determine whether the width of the first cardiac event is below a width threshold such that, if the width of the first cardiac event is narrower than the width threshold, and the close call threshold is crossed at a time when it is likely that a T-wave would occur, then it is found appropriate to declare a close call.

A seventh non-limiting example takes the form of a system as in the third non-limiting example, wherein the confirmation means further comprises matching means to determine whether the first cardiac event matches a template, wherein the confirmation means will only confirm that it is appropriate to declare a close call if the matching means finds a match between the first cardiac event and the template.

An eighth non-limiting example takes the form of a system as in either of the first or second non-limiting examples, wherein the close call means comprises confirmation means to confirm that it is appropriate to declare a close call if the width of the first cardiac event is narrower than a width threshold. A ninth non-limiting example takes the form of a system as in either of the first or second non-limiting examples, wherein the close call means comprises confirmation means to confirm that it is appropriate to declare a close call if the first cardiac event matches a template.

A tenth non-limiting example takes the form of a system as in any of the first nine non-limiting examples, which is further configured such that each cardiac event is intended to be a single cardiac cycle or beat. An eleventh non-limiting example takes the form of a system as in any of the first ten non-limiting examples, further comprising rhythm analysis means for determining whether a cardiac condition warranting therapy is occurring. A twelfth non-limiting example takes the form of a system as in any of the first eleven non-limiting examples, further comprising therapy means for delivering therapy if a cardiac condition warranting therapy is occurring.

A thirteenth non-limiting example takes the form of a system as in any of the first twelve non-limiting examples, wherein the system is configured as an transvenous implantable cardiac therapy system. A fourteenth non-limiting example takes the form of a system as in any of the first twelve non-limiting examples, wherein the system is configured as a subcutaneous implantable cardiac therapy system. A fifteenth non-limiting example takes the form of a system as in any of the first ten non-limiting examples, wherein the system is an implantable cardiac monitor.

A sixteenth non-limiting example takes the form of an implantable cardiac system comprising a plurality of electrodes coupled to operational circuitry configured to analyze cardiac signals, wherein: the operational circuitry is configured detect to cardiac events by the application of a detection threshold to a cardiac signal received from the electrodes, the detection threshold being defined by a detection profile selected from at least first and second detection profiles, with the second detection profile having lesser sensitivity to cardiac signals than the first detection profile; the operational circuitry is configured to detect a first cardiac event and determine whether a close call has occurred by applying close call rules; the operational circuitry is configured such that the close call rules comprise a first rule relying on a close call threshold defined relative to the detection threshold such that the first rule is met if the cardiac signal following the first cardiac event crosses the close call threshold without crossing the detection threshold; and the operational circuitry is configured to select the second detection profile for use in detecting at least one cardiac event after the first cardiac event if it determines that a close call has occurred in which at least the first rule has been met.

A seventeenth non-limiting example takes the form of a system as in the sixteenth non-limiting example, wherein the operational circuitry is configured to detect a second cardiac event after the first cardiac event and, if a close call has occurred between the first and second cardiac events, to apply the second detection profile following the second cardiac event in order to detect a third cardiac event after the second cardiac event, wherein each cardiac event is intended to be a single cardiac cycle or beat.

An eighteenth non-limiting example takes the form of a system as in the sixteenth or seventeenth non-limiting examples, wherein the operational circuitry is configured such that the close call rules comprise a second rule to determine whether, if the close call threshold is crossed after the first cardiac event, the time at which such crossing occurs corresponds to a likely T-wave would occur using an accepted formula for determining a QT Interval and assuming the first cardiac event represents a QRS complex, wherein if the close call threshold is crossed and the timing of the crossing corresponds to a likely T-wave, then it is found appropriate to declare a close call. A nineteenth non-limiting example takes the form of a system as in the eighteenth non-limiting example, wherein the accepted formula is selected from the group consisting of Fridericia's formula, Bazett's formula, or the Sagie et al. regression formula.

A twentieth non-limiting example takes the form of a system as in the sixteenth or seventeenth non-limiting examples, wherein the operational circuitry is configured such that the close call rules comprise a second rule to determine whether the first cardiac event has a width that is narrower than width threshold such that, if the close call threshold is crossed, and the width of the first cardiac event is narrower than the width threshold, then it is found appropriate to declare a close call.

A twenty-first non-limiting example takes the form of a system as in the sixteenth or seventeenth non-limiting examples, wherein the operational circuitry is configured such that the close call rules comprise a second rule to determine whether the first cardiac event matches a template, wherein if the close call threshold is crossed and the first cardiac event matches the template, then it is found appropriate to declare a close call.

A twenty-second non-limiting example takes the form of a method of operation in an implantable cardiac system comprising a plurality of electrodes coupled to operational circuitry configured to analyze cardiac signals, the method comprising: the operational circuitry detecting a first cardiac event by comparing a cardiac signal received from the electrodes to a detection threshold, the detection threshold being defined by a detection profile chosen from at least first and second detection profiles, with the second detection profile having lesser sensitivity to cardiac signals than the first detection profile; the operational circuitry detecting a close call after the first cardiac event, in which the close call is detected by applying a set of close call rules including a first rule in which: the operational circuitry defines a detection threshold to apply after the first cardiac event is detected; the operational circuitry defines a close call threshold below the detection threshold; and the operational circuitry determines that the close call threshold has been crossed without the detection threshold being crossed; and the operational circuitry determining that a close call has occurred in response to the set of close call rules being met, including finding that at least the first rule has been met, and, in response to determining that a close call has occurred, selects the second detection profile for use in detecting at least one cardiac event.

A twenty-third non-limiting example takes the form of a method as in the twenty-second non-limiting example, further comprising: the operational circuitry detecting a second cardiac event after the first cardiac event; the operational circuitry determining that the close call occurred between the first and second cardiac events; and in response to the close call, the operational circuitry applying the second detection profile following the second cardiac event in order to detect a third cardiac event after the second cardiac event; wherein each cardiac event is intended to be a single cardiac cycle or beat.

A twenty-fourth non-limiting example takes the form of a method as in either of the twenty-second or twenty-third non-limiting examples, further comprising the operational circuitry analyzing a second rule in the close call rules including: determining that the close call threshold is crossed after the first cardiac event; analyzing a time at which the crossing of the close call threshold occurred to determine whether it corresponds to a likely T-wave using an accepted formula for determining a QT Interval and assuming the first cardiac event represents a QRS complex; wherein the step of the operational circuitry detecting the close call includes determining that the second rule has been met by finding that the crossing of the close call threshold corresponds to a likely T-wave.

A twenty-fifth non-limiting example takes the form of a method as in the twenty-fourth non-limiting example wherein the operational circuitry is configured such that the accepted formula is selected from the group consisting of Fridericia's formula, Bazett's formula, or the Sagie et al. regression formula.

A twenty-sixth non-limiting example takes the form of a method as in either of the twenty-second or twenty-third non-limiting examples, further comprising the operational circuitry analyzing a second rule in the close call rules including: determining a width of the first cardiac event; and comparing the width of the first cardiac event to a width threshold; and wherein the step of the operational circuitry detecting the close call includes determining that the second rule has been met by finding that the width of the first cardiac event is narrower than the width threshold.

A twenty-seventh non-limiting example takes the form of a method as in either of the twenty-second or twenty-third non-limiting examples, further comprising the operational circuitry analyzing a second rule in the close call rules including comparing the first cardiac event to a template; and wherein the step of the operational circuitry detecting the close call includes determining that the second rule has been met by finding that the first cardiac event matches the template.

A twenty-eighth non-limiting example takes the form of a method of cardiac event detection in an implantable cardiac system having a plurality of electrodes and operational circuitry for the system coupled to the plurality of electrodes, the method comprising: the operational circuitry receiving a signal from the plurality of electrodes; and the operational circuitry detecting a plurality of cardiac events by comparing the signal to a detection threshold defined by a detection profile, the detection profile having: a refractory period applied initially after a cardiac event is detected during which additional cardiac events cannot be detected followed by one or more detection periods during which additional cardiac events can be detected if the cardiac signal crosses the detection threshold; wherein for at least one of the detection periods applied after a refractory period of a first of the plurality of detected cardiac events, the detection threshold is set by observing a signal peak during a corresponding detection period applied after a second of the plurality of detected cardiac events and adding a margin; and wherein the first of the plurality of detected cardiac events follows the second of the plurality of detected cardiac events.

A twenty-ninth non-limiting example takes the form of a method as in the twenty-eighth non-limiting example, wherein the detection threshold during the at least one detection period is set by observing the signal peak during the corresponding detection period after the second detected event and adding a margin only if the signal peak during the corresponding detection period after the second detected event also matches a signal peak during the corresponding detection period after a third detected event.

A thirtieth non-limiting example takes the form of an implantable cardiac system having a plurality of electrodes and operational circuitry for the system coupled to the plurality of electrodes, in which the operational circuitry is configured to perform the method of any of the twenty-second to twenty-ninth non-limiting examples.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A method of cardiac event detection in an implantable cardiac system having a plurality of electrodes and operational circuitry for the system coupled to the plurality of electrodes, the method comprising:
the operational circuitry receiving a signal from the plurality of electrodes; and
the operational circuitry detecting a plurality of cardiac events by comparing the signal to a detection threshold defined by a detection profile, the detection profile having:
a refractory period applied initially after a cardiac event is detected during which additional cardiac events cannot be detected; and
following the refractory period, at least a first detection period having a constant threshold, and a second detection period following the first detection period having a decaying threshold during which first and second detection periods additional cardiac events can be detected if the cardiac signal crosses the detection threshold;
wherein for the first detection period applied after a refractory period of a first of the plurality of detected cardiac events, the detection threshold is set by observing a signal peak during a corresponding first detection period applied after a refractory period of a second of the plurality of detected cardiac events, and adding a margin to the observed signal peak; and
wherein the first of the plurality of detected cardiac events follows the second of the plurality of detected cardiac events, and the first detection period precedes the second detection period.

2. The method of claim 1 wherein the signal peak to which a margin is added does not cross the detection threshold.

3. The method of claim 1, further comprising calculating the margin relative to the amplitude of a peak of the second of the plurality of cardiac events that occurs during the refractory period.

4. The method of claim 1 wherein the operational circuitry is contained in a pulse generator for an implantable defibrillator, and the method further comprises analyzing the detected cardiac events to determine whether cardiac defibrillation is needed and if so, delivering a defibrillation stimulus.

5. The method of claim 1 wherein the operational circuitry and the plurality of electrodes form parts of an implantable cardiac monitor, and the method further comprises determining whether a likely arrhythmia is taking place and, if so, recording data in the implantable cardiac monitor for later retrieval.

6. The method of claim 1 wherein the operational circuitry and the plurality of electrodes form parts of an implantable cardiac monitor, and the method further comprises determining whether a likely arrhythmia is taking place and, if so, issuing a warning to the patient.

7. An implantable cardiac system comprising a plurality of electrodes coupled to operational circuitry configured to analyze cardiac signals, wherein:
the operational circuitry is configured to receive the cardiac signals from the plurality of electrodes; and
the operational circuitry is configured to detect a plurality of cardiac events by comparing the cardiac signals to a detection threshold defined by a detection profile, the detection profile having:
a refractory period applied initially after a cardiac event is detected during which additional cardiac events cannot be detected; and
following the refractory period, at least a first detection period having a constant threshold, and a second detection period following the first detection period having a decaying threshold during which additional cardiac events can be detected if the cardiac signal crosses the detection threshold;
wherein for the first detection period applied after a refractory period of a first of the plurality of detected cardiac events, the operational circuitry is configured to observe a signal peak during a corresponding first detection period applied after a refractory period of a second of the plurality of detected cardiac events and add a margin to the signal peak to calculate the detection threshold usable during the first detection period; and
wherein the first of the plurality of detected cardiac events follows the second of the plurality of detected cardiac events, and the first detection period precedes the second detection period.

8. The system of claim 7 wherein the signal peak to which the margin is added does not cross the detection threshold.

9. The system of claim 7, wherein the operational circuitry is further configured to calculate the margin relative to the amplitude of a peak occurring during the refractory period of the second of the plurality of detected cardiac events.

10. The system of claim 7 further comprising a housing containing the operational circuitry and a lead having the electrodes thereon, wherein the lead is coupled to the housing to electrically link the electrodes to the operational circuitry, wherein the housing further contains defibrillation therapy circuitry for generating and outputting defibrillation therapy using the lead and the housing, further wherein the operational circuitry is configured to analyze the plurality of detected events to determine whether therapy is needed and, if so, to deliver the needed therapy.

11. The system of claim 7 further comprising a housing containing the operational circuitry and having at least one electrode thereon, wherein the system is configured as an implantable cardiac monitor and the operational circuitry is configured to analyze the plurality of detected events to determine whether a likely arrhythmia is taking place and, if so, to record data for later retrieval.

12. The system of claim 7 further comprising a housing containing the operational circuitry and having at least one electrode thereon, wherein the system is configured as an implantable cardiac monitor and the operational circuitry is configured to analyze the plurality of detected events to determine whether a likely arrhythmia is taking place and, if so, to issue a warning to a recipient of the implantable cardiac monitor.

* * * * *